（12）United States Patent
Sumida et al.

(10) Patent No.: US 11,653,821 B2
(45) Date of Patent: May 23, 2023

(54) ENDOSCOPE AND HANDLE OPERATION UNIT

(71) Applicants: NIREC CORPORATION, Kochi (JP); MIZUHO CORPORATION, Tokyo (JP)

(72) Inventors: Tetsuo Sumida, Kochi (JP); Hiromi Sato, Kochi (JP); Haruyasu Katahira, Kanagawa (JP); Ichiro Kitani, Tokyo (JP)

(73) Assignees: NIREC CORPORATION, Kochi (JP); MIZUHO CORPORATION, Tokyo (JP)

( * ) Notice: Subject to any disclaimer, the term of this patent is extended or adjusted under 35 U.S.C. 154(b) by 0 days.

(21) Appl. No.: 17/830,705

(22) Filed: Jun. 2, 2022

(65) Prior Publication Data
US 2022/0386850 A1 Dec. 8, 2022

(30) Foreign Application Priority Data
Jun. 2, 2021 (JP) .............................. JP2021-092923

(51) Int. Cl.
*A61B 1/005* (2006.01)
*A61B 1/05* (2006.01)
*A61B 1/00* (2006.01)

(52) U.S. Cl.
CPC .......... *A61B 1/0052* (2013.01); *A61B 1/0057* (2013.01); *A61B 1/00066* (2013.01); *A61B 1/00096* (2013.01); *A61B 1/05* (2013.01)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS 3,896,793 A * 7/1975 Mitsui ................ A61B 1/00165
600/173
4,911,148 A * 3/1990 Sosnowski ......... A61B 1/00165
600/164
(Continued)

FOREIGN PATENT DOCUMENTS

JP 4458221 B2 4/2010
JP 5599583 B2 10/2014
(Continued)

*Primary Examiner* — Ryan N Henderson
(74) *Attorney, Agent, or Firm* — Paratus Law Group, PLLC

(57) ABSTRACT

An endoscope includes a handle operation unit. The handle operation unit includes: an outer ring; a cam ring accommodated in the outer ring to rotate in accordance with rotation of the outer ring about a central axis and having a pair of guide holes; a pair of slide members accommodated in the respective guide holes and fixed to a force transmission member; and a support portion having a pair of slide grooves extending along a longitudinal direction of the endoscope, the support portion being accommodated in the cam ring to support the pair of slide members. The slide members slide in the respective slide grooves in accordance with the rotation of the outer ring. The field of view of the image-capturing unit is changed in accordance with sliding of the pair of slide members.

12 Claims, 7 Drawing Sheets

(58) Field of Classification Search
CPC ... A61B 1/0056; A61B 1/0057; A61B 1/0058; A61B 1/00098; A61B 1/00173; A61B 2017/003; A61B 2017/00318; A61B 2017/00323; A61B 2017/00327; A61B 1/00066; A61B 1/00096; A61M 25/0133; A61M 25/0136; A61M 25/0147

See application file for complete search history.

(56) References Cited

U.S. PATENT DOCUMENTS

| | | | | |
|---|---|---|---|---|
| 5,885,208 | A * | 3/1999 | Moriyama | A61B 1/0051 600/146 |
| 6,179,809 | B1 * | 1/2001 | Khairkhahan | A61M 25/0147 604/95.04 |
| 6,554,794 | B1 * | 4/2003 | Mueller | A61M 25/0141 604/95.04 |
| 6,560,013 | B1 | 5/2003 | Ramsbottom | |
| 7,491,166 | B2 * | 2/2009 | Ueno | A61B 1/018 600/129 |
| 9,572,478 | B2 | 2/2017 | Hoeg | |
| 2002/0099266 | A1 * | 7/2002 | Ogura | A61B 1/0055 600/139 |
| 2004/0267090 | A1 * | 12/2004 | Ueno | A61B 1/018 600/106 |
| 2007/0260223 | A1 * | 11/2007 | Scheibe | A61M 25/0136 604/528 |
| 2009/0090764 | A1 * | 4/2009 | Viola | A61B 17/07207 227/176.1 |
| 2010/0022838 | A1 | 1/2010 | Hoeg | |
| 2010/0076433 | A1 * | 3/2010 | Taylor | A61B 18/1445 606/170 |
| 2011/0040308 | A1 * | 2/2011 | Cabrera | A61B 1/00087 606/144 |
| 2014/0012080 | A1 | 1/2014 | Wada et al. | |
| 2014/0249369 | A1 * | 9/2014 | Hanabusa | A61B 1/051 600/109 |
| 2017/0127910 | A1 * | 5/2017 | Asaoka | A61B 1/0055 |
| 2017/0156747 | A1 * | 6/2017 | Worrell | A61B 17/2816 |
| 2017/0280980 | A1 | 10/2017 | Yasunaga et al. | |
| 2018/0071490 | A1 * | 3/2018 | Khuu | F16H 25/16 |
| 2018/0249894 | A1 | 9/2018 | Kolberg et al. | |
| 2021/0196251 | A1 * | 7/2021 | Dull | A61M 25/0102 |
| 2021/0361912 | A1 * | 11/2021 | Matlock | A61B 17/24 |
| 2022/0047149 | A1 | 2/2022 | Kolberg et al. | |

FOREIGN PATENT DOCUMENTS

| | | |
|---|---|---|
| JP | 2015-070953 A | 4/2015 |
| JP | 5898274 B2 | 4/2016 |
| JP | 2016-174947 A | 10/2016 |
| JP | 6116780 B1 | 4/2017 |
| JP | 2020-179230 A | 11/2020 |

* cited by examiner

ENDOSCOPE AND HANDLE OPERATION UNIT

CROSS-REFERENCE TO RELATED APPLICATIONS

This application is based on and claims priority under 35 USC 119 from Japanese Patent Application No. 2021-092923 filed on Jun. 2, 2021, the contents of which are incorporated herein by reference.

TECHNICAL FIELD

The present disclosure relates to an endoscope and a handle operation unit configured to change a field of view of the endoscope.

BACKGROUND ART

JP-A-2015-070953 discloses an endoscope where handle levers (a left-right lever and an up-down lever) are provided in an operation unit. According to the endoscope, a medical worker can adjust a field of view of an image-capturing unit provided at a tip end portion of a rigid tube by operating each handle lever.

SUMMARY OF INVENTION

On the other hand, according to the above-described endoscope, skill is required to appropriately adjust the field of view of the image-capturing unit by an operation performed on the handle lever, and it is difficult to appropriately adjust the field of view of the image-capturing unit by an intuitive operation performed on the handle lever. In addition, it is sufficiently assumed that there may be a situation where the field of view of the image-capturing unit is unintentionally changed due to unintended contact with the handle lever. From the above viewpoint, there is room for consideration in terms of further improving usability of the endoscope (in particular, a handle operation unit of the endoscope).

An object of the present disclosure is to provide an endoscope and a handle operation unit with further improved usability.

The present disclosure provides an endoscope including: a scope; an image-capturing unit accommodated in the scope, the image-capturing unit being configured to capture an image of an object; a handle operation unit configured to change a field of view of the image-capturing unit in accordance with an operation of a user; and a force transmission member accommodated in the scope and fixed to the handle operation unit and the scope. The handle operation unit includes: an outer ring configured to be operated by the user; a cam ring accommodated in the outer ring so as to rotate in accordance with rotation of the outer ring about a central axis of the handle operation unit, the cam ring having a pair of guide holes; a pair of slide members, each of the pair of slide members being accommodated in a corresponding one of the pair of guide holes and fixed to the force transmission member; and a support portion having a pair of slide grooves extending along a longitudinal direction of the endoscope, the support portion being accommodated in the cam ring to support the pair of slide members. Each of the pair of slide members is slidable in a corresponding one of the pair of slide grooves. Each of the pair of slide members slides in the corresponding one of the pair of slide grooves in accordance with the rotation of the outer ring about the central axis. The field of view of the image-capturing unit is changed in accordance with sliding of the pair of slide members.

According to the above configuration, the pair of slide members are slid in the slide grooves by the rotation of the outer ring in accordance with the operation of the user, and as a result, the field of view of the image-capturing unit is changed. Therefore, the user can relatively easily adjust the field of view of the image-capturing unit by an intuitive rotation operation performed on the handle operation unit. In addition, since it is not necessary to provide any field-of-view adjustment lever or the like for adjusting the field of view of the image-capturing unit in the handle operation unit, a size of the handle operation unit can be reduced, and it is possible to further simplify and improve appearance of the handle operation unit. Further, since the handle operation unit is not provided with any field-of-view adjustment lever, it is possible to prevent a situation where the field of view of the image-capturing unit is unintentionally changed due to unintended contact with the field-of-view adjustment lever. Therefore, an endoscope whose usability is further improved can be provided.

The scope may include a movable portion configured to be inclined relative to an up-down direction or a left-right direction perpendicular to the longitudinal direction, the image-capturing unit may be accommodated in the movable portion, the force transmission member may be fixed to the movable portion, the movable portion may be inclined relative to the up-down direction or the left-right direction in accordance with sliding of the pair of slide members, and the field of view of the image-capturing unit may be changed in accordance with inclination of the movable portion.

According to the above configuration, the pair of slide members are slid in the slide grooves by the rotation of the outer ring in accordance with the operation of the user, and thereafter, the movable portion in which the image-capturing unit is accommodated is inclined relative to the up-down direction or the left-right direction, and as a result, the field of view of the image-capturing unit is changed. In this way, the field of view of the image-capturing unit can be adjusted by an intuitive rotation operation performed on the handle operation unit.

As the cam ring rotates, one of the pair of slide members may slide in one of the pair of slide grooves in a first direction while the other of the pair of slide members slides in the other of the pair of slide grooves in a second direction that is opposite to the first direction.

According to the above configuration, the pair of slide members slide in directions opposite to each other, so that the field of view of the image-capturing unit can be changed via the force transmission member.

When the one of the pair of slide members slides in the first direction in the one of the pair of slide grooves, the force transmission member fixed to the one of the pair of slide members may be pulled in the first direction, and when the other of the pair of slide members slides in the second direction in the other of the pair of slide grooves, the force transmission member fixed to the other of the pair of slide members may be loosened.

According to the above configuration, the force transmission member fixed to the one of the pair of slide members is pulled in the first direction while the force transmission member fixed to the other of the pair of slide members is loosened. In this way, it is possible to change the field of view of the image-capturing unit via the force transmission member fixed to each of the pair of slide members.

The pair of guide holes may extend along a direction that is inclined relative to the longitudinal direction of the endoscope.

According to the above configuration, as the cam ring rotates about the central axis of the handle operation unit, each of the pair of slide members can successfully slide in the corresponding slide groove.

Each of the pair of slide members may include: a slide pin accommodated in the corresponding one of the pair of guide holes; and a slide holder holding the slide pin, the slide holder being slidable in the corresponding one of the pair of slide grooves. The slide holder may be fixed to the force transmission member.

According to the above configuration, the slide pin is accommodated in the guide hole, and the slide holder holding the slide pin is fixed to the force transmission member. Therefore, it is possible to change the field of view of the image-capturing unit through tension acting on the force transmission member in accordance with the rotation of the cam ring about the central axis of the handle operation unit.

One of the outer ring and the cam ring may include an engagement protrusion portion protruding toward the other of the outer ring and the cam ring, and the other of the outer ring and the cam ring may have an engagement recess portion configured to engage the engagement protrusion portion.

According to the above configuration, since the outer ring and the cam ring are engaged with each other via the engagement protrusion portion and the engagement recess portion, the cam ring can be reliably rotated in accordance with the rotation of the outer ring.

The image-capturing unit may include: an image sensor configured to generate image data of the object; and an optical member that is optically connected to the image sensor, the image sensor being configured to guide light associated with the object to the image sensor.

The image-capturing unit may further include a light emission unit configured to emit light toward the object. The field of view of the image-capturing unit and an emission direction of the light emitted from the light emission unit may be changed in accordance with the rotation of the outer ring about the central axis.

According to the above configurations, the user can relatively easily adjust the field of view of the image-capturing unit and the emission direction of the light by an intuitive rotation operation performed on the handle operation unit.

The present disclosure provides an endoscope including: a scope; an image-capturing unit accommodated in the scope, the image-capturing unit being configured to capture an image of an object; a handle operation unit configured to change a field of view of the image-capturing unit in accordance with an operation of a user; and a force transmission member accommodated in the scope and fixed to the handle operation unit. The handle operation unit includes: an outer ring configured to be operated by the user; a cam ring accommodated in the outer ring so as to rotate in accordance with rotation of the outer ring about a central axis of the handle operation unit, the cam ring having a pair of guide holes; a pair of slide members, each of the pair of slide members being accommodated in a corresponding one of the pair of guide holes and fixed to the force transmission member; and a support portion having a pair of slide grooves extending along a longitudinal direction of the endoscope, the support portion being accommodated in the cam ring to support the pair of slide members. Each of the pair of slide members is slidable in a corresponding one of the pair of slide grooves. Each of the pair of slide members slides in the corresponding one of the pair of slide grooves in accordance with the rotation of the outer ring about the central axis. The field of view of the image-capturing unit is changed in accordance with sliding of the pair of slide members.

The present disclosure provides a handle operation unit configured to change a field of view of an endoscope in accordance with an operation of a user, the handle operation unit including: an outer ring configured to be operated by the user; a cam ring accommodated in the outer ring so as to rotate in accordance with rotation of the outer ring about a central axis of the handle operation unit, the cam ring having a pair of guide holes; a pair of slide members, each of the pair of slide members being accommodated in a corresponding one of the pair of guide holes and fixed to a force transmission member; and a support portion having a pair of slide grooves extending along a longitudinal direction of the endoscope, the support portion being accommodated in the cam ring to support the pair of slide members. Each of the pair of slide members is slidable in a corresponding one of the pair of slide grooves. Each of the pair of slide members slides in the corresponding one of the pair of slide grooves in accordance with the rotation of the outer ring about the central axis. The field of view of the endoscope is changed in accordance with sliding of the pair of slide members.

According to the above configuration, the pair of slide members are slid in the slide grooves by the rotation of the outer ring in accordance with the operation of the user, and as a result, the field of view of the endoscope is changed. Therefore, the user can relatively easily adjust the field of view of the endoscope by an intuitive rotation operation performed on the handle operation unit. In addition, since it is not necessary to provide any field-of-view adjustment lever or the like for adjusting the field of view of the endoscope in the handle operation unit, a size of the handle operation unit can be reduced, and it is possible to further simplify and improve appearance of the handle operation unit. Further, since no field-of-view adjustment lever is provided in the handle operation unit, it is possible to prevent a situation where the field of view of the endoscope is unintentionally changed due to unintended contact with the field-of-view adjustment lever. Therefore, a handle operation unit whose usability is further improved can be provided.

According to the present disclosure, the endoscope and the handle operation unit with further improved usability can be provided.

DESCRIPTION OF EMBODIMENTS

Figure 1:
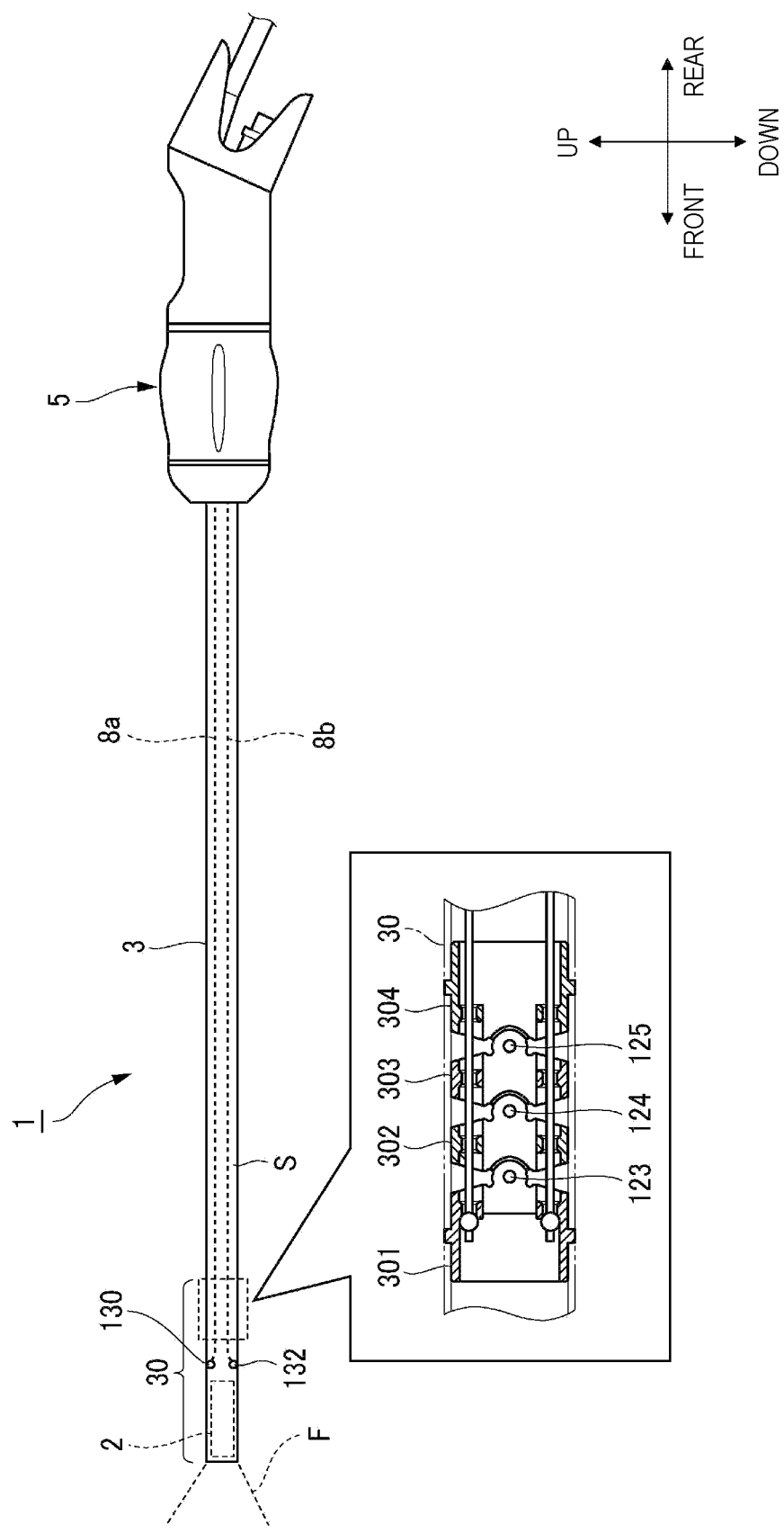
FIG. 1 is an overall view of an endoscope according to an embodiment.

Hereinafter, an endoscope 1 according to an embodiment of the present disclosure (hereinafter, simply referred to as "the present embodiment") will be described with reference to the drawings. Dimensions of respective members shown in the drawings may be different from actual dimensions of the respective members for convenience of description.

In addition, in the description of the present embodiment, for convenience of description, a front-rear direction, an up-down direction, and a left-right direction of the endoscope 1 may be referred to as appropriate. These directions are relative directions set for the endoscope 1 shown in FIG. 1. Although the left-right direction is not shown in FIG. 1, the left-right direction is a direction perpendicular to the up-down direction and the front-rear direction. It is assumed that any one of the front-rear direction, the up-down direction, and the left-right direction is orthogonal to the other two directions. The front-rear direction corresponds to a longitudinal direction of the endoscope 1 (in particular, a scope 3 of the endoscope 1). The front-rear direction is a direction including a forward direction and a rearward direction. The up-down direction is a direction including an upward direction and a downward direction. The left-right direction is a direction including a leftward direction and a rightward direction.

First, a configuration of the endoscope 1 according to the present embodiment will be described below with reference to FIG. 1. FIG. 1 is an overall view showing the endoscope 1 according to the present embodiment.

As shown in FIG. 1, the endoscope 1 includes the scope 3, an image-capturing unit 2, and a handle operation unit 5. The endoscope 1 may be a medical endoscope or an industrial endoscope (for example, an endoscope for observing an inside of a containment vessel of a nuclear power plant). In a case where the endoscope 1 is a medical endoscope, a medical worker who is a user can observe a biological tissue (an example of an object) such as an internal organ of a patient in real time by inserting the endoscope 1 into a body of the patient. The endoscope 1 may be, for example, a rigid endoscope used under laparoscopic surgery.

In addition, both visible light image data and near-infrared image data of the biological tissue of the patient can be simultaneously acquired through the endoscope 1. In this regard, under the laparoscopic surgery, a fluorescent contrast agent that emits near-infrared light, such as indocyanine green (ICG), is used. When the ICG is irradiated with excitation light (laser light), the ICG emits near-infrared light. A center wavelength λ of the laser light that serves as the excitation light is, for example, in a range of 700 nm to 800 nm, more specifically, in a range of 785 nm to 795 nm. After injecting the ICG into a vein of the patient, the medical worker can reliably specify an affected part where the ICG remains by visually recognizing the near-infrared light image data acquired through the endoscope 1. In this way, the medical worker such as an external physician can perform a surgical treatment (such as resection of the affected part) on the affected part specified by the ICG.

The scope 3 corresponds to a portion of the endoscope 1 to be inserted into the body of the patient. The scope 3 extends in the front-rear direction, and is configured as, for example, a rigid tube including a space S. An outer diameter of the scope 3 is, for example, about 10 mm, and an inner diameter of the scope 3 is, for example, about 9 mm. The scope 3 includes a movable portion 30 that is inclined relative to the up-down direction.

Figure 7A:
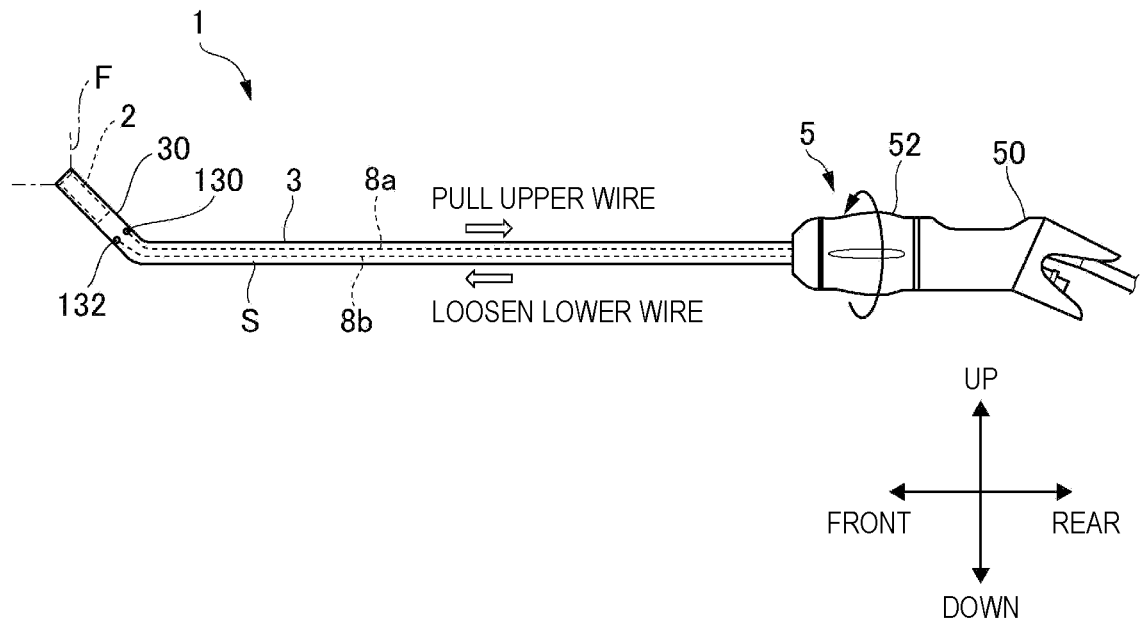
FIG. 7A shows a state where the movable portion of the scope is inclined obliquely upward in accordance with counterclockwise rotation of an outer ring.
Figure 7B:
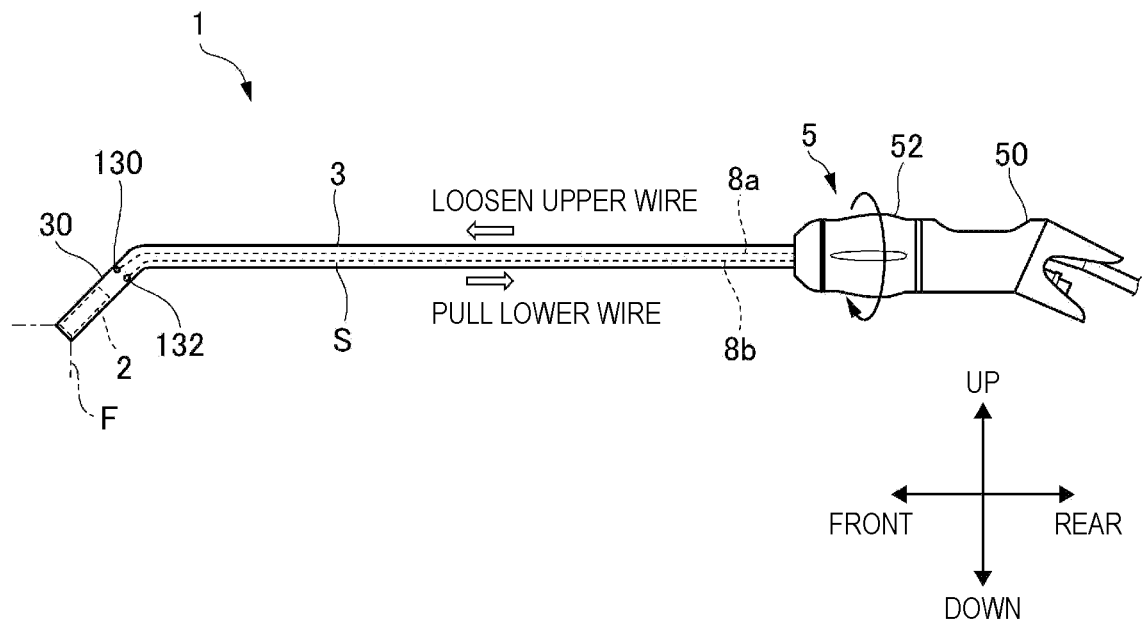
FIG. 7B shows a state where the movable portion of the scope is inclined obliquely downward in accordance with clockwise rotation of the outer ring.

The movable portion 30 is configured to be inclined obliquely upward or obliquely downward in accordance with a rotation operation of the medical worker performed on the handle operation unit 5 (see FIGS. 7A and 7B). In an enlarged cross-sectional view of a part of the movable portion 30 shown in FIG. 1, the movable portion 30 includes a plurality of movable connection elements 301 to 304 aligned in the front-rear direction. The movable connection element 301 is rotatably fixed to the movable connection element 302 through a movable shaft 123. The movable connection element 302 is rotatably fixed to the movable connection element 303 through a movable shaft 124. The movable connection element 303 is rotatably fixed to the movable connection element 304 through a movable shaft 125. In this way, when one of wires 8a and 8b is pulled rearward, the movable portion 30 can be inclined relative to the up-down direction by the plurality of movable connection elements 301 to 304.

The two wires 8a and 8b (an example of a force transmission member) are accommodated in the scope 3. The wires 8a and 8b extend in the front-rear direction from the handle operation unit 5 to the movable portion 30 of the scope 3. The upper wire 8a is fixed to the handle operation unit 5 and is fixed to the movable portion 30 by a fixing pin 130. The lower wire 8b is fixed to the handle operation unit 5 and is fixed to the movable portion 30 by a fixing pin 132. As will be described later, the movable portion 30 is inclined obliquely upward in a state where the wire 8a is pulled rearward, and the movable portion 30 is inclined obliquely downward in a state where the wire 8b is pulled rearward. Although the wires are used as the example of the force transmission member that transmits a force to the movable portion 30 in the present embodiment, the force transmission member is not limited to the wires. For example, belts or cables may also be used as the force transmission member.

The image-capturing unit 2 is configured to capture an image of the biological tissue by receiving visible light and near-infrared light associated with the biological tissue of the patient. Specifically, the image-capturing unit 2 is configured to capture the image of the biological tissue by receiving visible light reflected by the biological tissue of the patient and near-infrared light emitted from the fluorescent contrast agent (ICG or the like) remaining in the biological tissue. In the present embodiment, the image-capturing unit 2 is accommodated in the space S of the scope 3. In this regard, the image-capturing unit 2 is downsized to such an extent that the image-capturing unit 2 can be accommodated in the scope 3 whose inner diameter is about 9 mm. In addition, the image-capturing unit 2 is disposed in the vicinity of a tip end of the scope 3. The tip end of the scope 3 faces the biological tissue of the patient in a state where the endoscope 1 is inserted into the body of the patient.

(Specific Configuration of Image-Capturing Unit)

Figure 2:
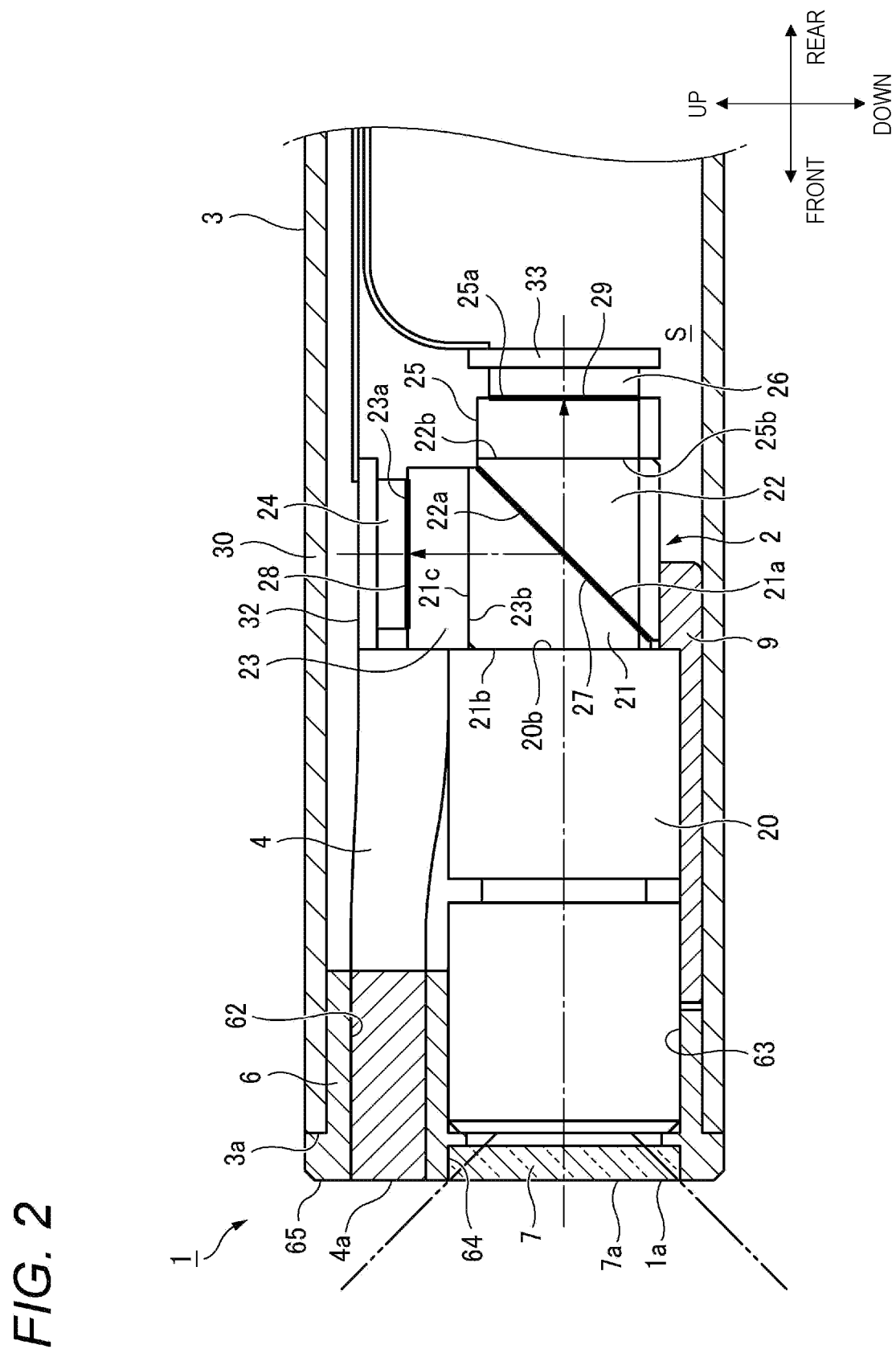
FIG. 2 is a cross-sectional view showing an example of an image-capturing unit.

Next, a specific configuration of the image-capturing unit 2 will be described below with reference to FIG. 2. FIG. 2 is a cross-sectional view (a cross-sectional view perpendicular to the left-right direction) showing an example of the image-capturing unit 2. As shown in FIG. 2, the image-capturing unit 2 includes a light guide 4, a first support member 9, a second support member 6, and a lens cover 7. The image-capturing unit 2 further includes a lens unit 20, a first prism 21, a second prism 22, and a visible light reflection film 27. The image-capturing unit 2 further includes a first trimming filter 23, an infrared light blocking film 28, a first image sensor 24, and a first circuit board 32. The image-capturing unit 2 further includes a second trimming filter 25, a visible light blocking film 29, a second image sensor 26, and a second circuit board 33.

The light guide 4 (an example of a light emission unit) is configured to guide visible light emitted from a visible light source (not shown) and excitation light emitted from an excitation light source (not shown) toward the biological tissue of the patient. The light guide 4 includes a large number of optical fibers through which the visible light and the excitation light propagate. The light guide 4 is accommodated in the space S of the scope 3, and extends to the visible light source and the excitation light source along the front-rear direction. The visible light emitted from the light guide 4 is reflected by the biological tissue and then received by the first image sensor 24. In addition, the excitation light emitted from the light guide 4 is applied to the fluorescent contrast agent such as the ICG remaining in the biological tissue. Thereafter, near-infrared light (fluorescence) emitted from the fluorescent contrast agent through irradiation with the excitation light is received by the second image sensor 26.

The first support member 9 is configured to support the lens unit 20, the first prism 21, and the second prism 22 that function as optical members, and is fixed to the lens unit 20, the first prism 21, and the second prism 22 by an adhesive. The second support member 6 is fixed to the first support member 9 and the scope 3 by an adhesive. In addition, the second support member 6 includes an insertion hole 62 into which the light guide 4 is inserted, an insertion hole 63 into which the lens unit 20 is inserted, and an insertion hole 64 into which the lens cover 7 is inserted. In a state where the light guide 4 is inserted into the insertion hole 62, the light guide 4 is supported by the second support member 6. The insertion hole 63 and the insertion hole 64 communicate with each other. In a state where the lens cover 7 is inserted into the insertion hole 64, the lens cover 7 is fixed and supported by the second support member 6. A front surface 65 of the second support member 6, a front surface 7a of the lens cover 7, and an end surface 4a of the light guide 4 constitute a tip end surface 1a, which faces the biological tissue, of the endoscope 1.

The lens unit 20 is configured to guide the visible light and the near-infrared light associated with the biological tissue toward the first prism 21. In order to widen an angle of view (a view angle) of the image-capturing unit 2 and more efficiently take in the visible light and the near-infrared light from the biological tissue, it is preferable that the lens unit 20 is disposed in the vicinity of a tip end 3a of the scope 3 or in the vicinity of the tip end surface 1a of the endoscope 1. The lens unit 20 and the first prism 21 are fixed to each other via the first support member 9. In this regard, an emission surface 20b of the lens unit 20 and an incident surface 21b of the first prism 21 are in contact with each other.

The first prism 21 and the second prism 22 are configured as right-angle prisms. The first prism 21 and the second prism 22 are each formed of, for example, a transparent glass material or a transparent plastic material. The first prism 21 and the second prism 22 face each other and are fixed to each other by an adhesive. In particular, the first prism 21 and the second prism 22 are fixed to each other in a state where an inclined surface 21a of the first prism 21 and an inclined surface 22a of the second prism 22 face each other. The first prism 21 and the second prism 22 that are fixed to each other form a rectangular parallelepiped shape.

The visible light reflection film 27 is provided between the inclined surface 21a of the first prism 21 and the inclined surface 22a of the second prism 22. In the present embodiment, after the visible light reflection film 27 is formed on one of the inclined surface 21a and the inclined surface 22a, the first prism 21 and the second prism 22 are fixed to each other via the adhesive. The visible light reflection film 27 is configured to separate the visible light and the near-infrared light from the biological tissue. More specifically, the visible light reflection film 27 is configured to reflect the visible light that is emitted from the biological tissue and transmitted through the lens unit 20 and the first prism 21 toward the first trimming filter 23. Further, the visible light reflection film 27 is configured to transmit the near-infrared light that is emitted from the biological tissue and transmitted through the lens unit 20 and the first prism 21 toward the second trimming filter 25.

Since the inclined surface 21a of the first prism 21 and the inclined surface 22a of the second prism 22 are each inclined at 45 degrees relative to the front-rear direction, the visible light reflection film 27 is also inclined at 45 degrees relative to the front-rear direction. Therefore, the visible light reflection film 27 reflects the visible light in such a manner that a propagation direction of the visible light is changed by 90 degrees, and transmits the near-infrared light in such a manner that a propagation direction of the near-infrared light is not changed. In this way, the propagation direction of the visible light is converted from the front-rear direction to the up-down direction by the visible light reflection film 27, while the propagation direction of the near-infrared light traveling in the front-rear direction is not changed by the visible light reflection film 27.

The first trimming filter 23 is fixed to the first prism 21 by an adhesive. An incident surface 23b of the first trimming filter 23 and an emission surface 21c of the first prism 21 are in contact with each other via the adhesive. The first trimming filter 23 is configured to transmit visible light and block near-infrared light. The light reflected by the visible light reflection film 27 and transmitted through the first prism 21 is incident on the first trimming filter 23. The first trimming filter 23 transmits a visible light component of the incident light incident on the first trimming filter 23, and blocks a near-infrared light component of the incident light.

The infrared light blocking film 28 is provided between the first trimming filter 23 and the first image sensor 24 in the up-down direction. In the present embodiment, after the infrared light blocking film 28 is formed on an emission surface 23a of the first trimming filter 23, the first trimming filter 23 and the first image sensor 24 are fixed to each other via an adhesive. The infrared light blocking film 28 is configured to transmit visible light and block near-infrared light and excitation light applied to the biological tissue whose center wavelength is included in a wavelength band of 700 nm to 800 nm.

The first image sensor 24 is mounted on the first circuit board 32, and is arranged in such a manner that an image-capturing surface thereof faces the first trimming filter 23 and the infrared light blocking film 28 in the up-down direction. The first image sensor 24 is fixed to the first trimming filter 23 by an adhesive via the infrared light blocking film 28. The first image sensor 24 is configured to receive visible light transmitted through a visible light channel formed by a combination of the visible light reflection film 27, the first trimming filter 23, and the infrared light blocking film 28, and to convert the received visible light into an electric signal.

The second trimming filter 25 is fixed to the second prism 22 by an adhesive. An incident surface 25b of the second trimming filter 25 and an emission surface 22b of the second prism 22 are in contact with each other via the adhesive. The second trimming filter 25 is configured to transmit near-infrared light and block visible light. Light transmitted through the visible light reflection film 27 and the second prism 22 is incident on the second trimming filter 25. The second trimming filter 25 transmits a near-infrared light component of the incident light incident on the second trimming filter 25 and blocks a visible light component of the incident light.

The visible light blocking film 29 is provided between the second trimming filter 25 and the second image sensor 26 in the front-rear direction. In the present embodiment, after the visible light blocking film 29 is formed on an emission surface 25a of the second trimming filter 25, the second trimming filter 25 and the second image sensor 26 are fixed to each other via an adhesive. The visible light blocking film 29 is configured to transmit near-infrared light and block visible light and excitation light applied to the biological tissue whose center wavelength is included in the wavelength band of 700 nm to 800 nm. The visible light blocking film 29 transmits an infrared light component of incident light that is transmitted through the second trimming filter 25 and incident on the visible light blocking film 29, and blocks a visible light component of the incident light. In this way, the near-infrared light emitted from the fluorescent contrast agent existing in the biological tissue is incident on the second image sensor 26 through a near-infrared light channel formed by a combination of the visible light reflection film 27, the second trimming filter 25, and the visible light blocking film 29.

The second image sensor 26 is mounted on the second circuit board 33, and is arranged in such a manner that an image-capturing surface thereof faces the second trimming filter 25 and the visible light blocking film 29 in the front-rear direction. The second image sensor 26 is fixed to the second trimming filter 25 by an adhesive via the visible light blocking film 29. The second image sensor 26 is configured to receive infrared light transmitted through an infrared light channel formed by a combination of the visible light reflection film 27, the second trimming filter 25, and the visible light blocking film 29, and to convert the received infrared light into an electric signal.

(Specific Configuration of Handle Operation Unit)

Figure 3:
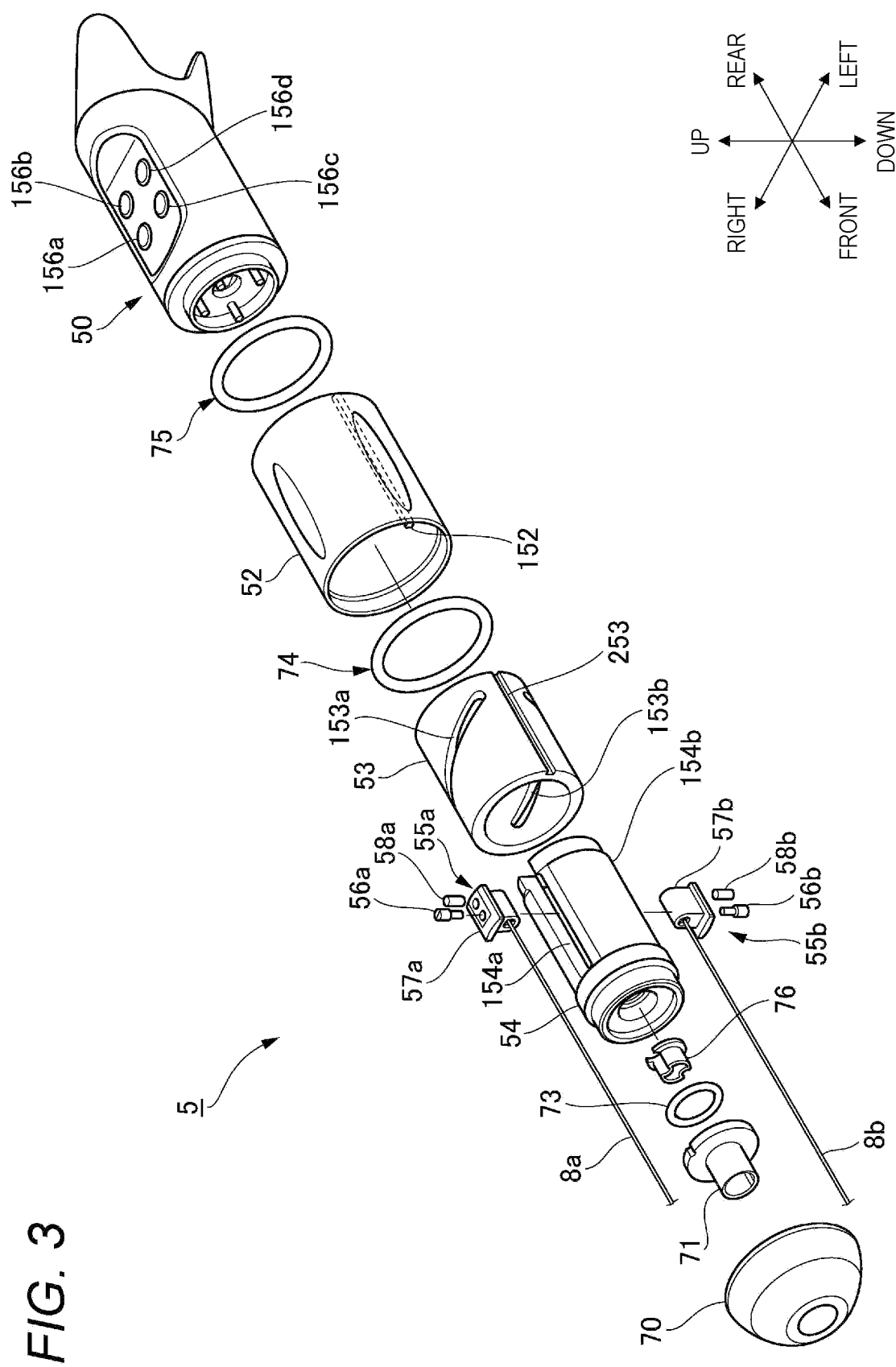
FIG. 3 is an exploded perspective view of a handle operation unit.
Figure 4A:
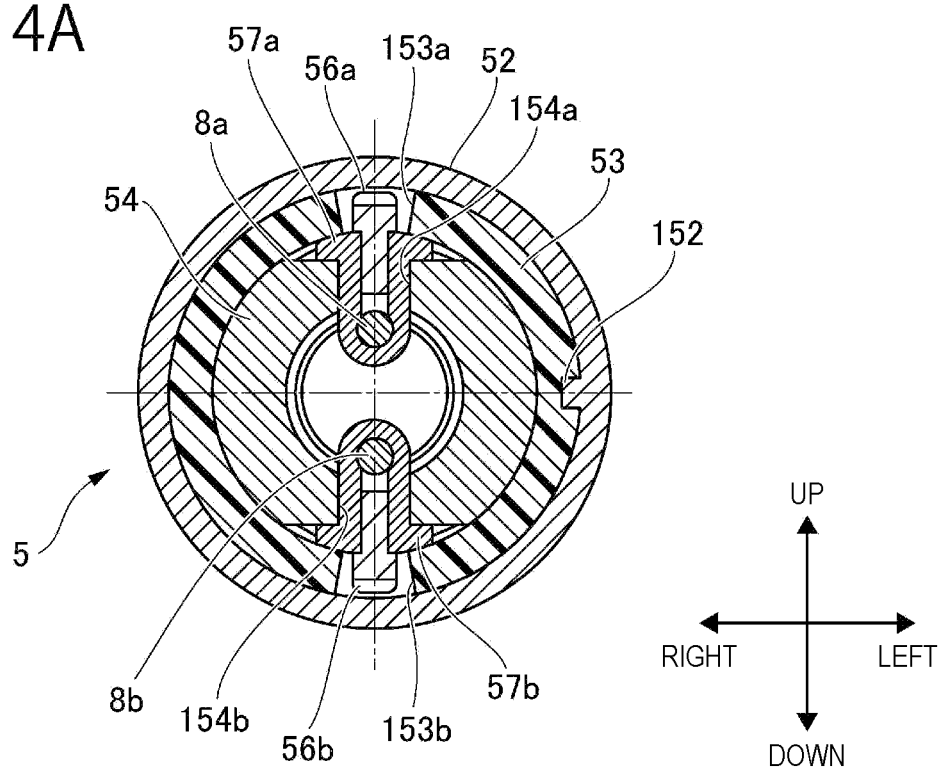
FIG. 4A is a cross-sectional view of the handle operation unit taken along a plane perpendicular to a front-rear direction.
Figure 4B:
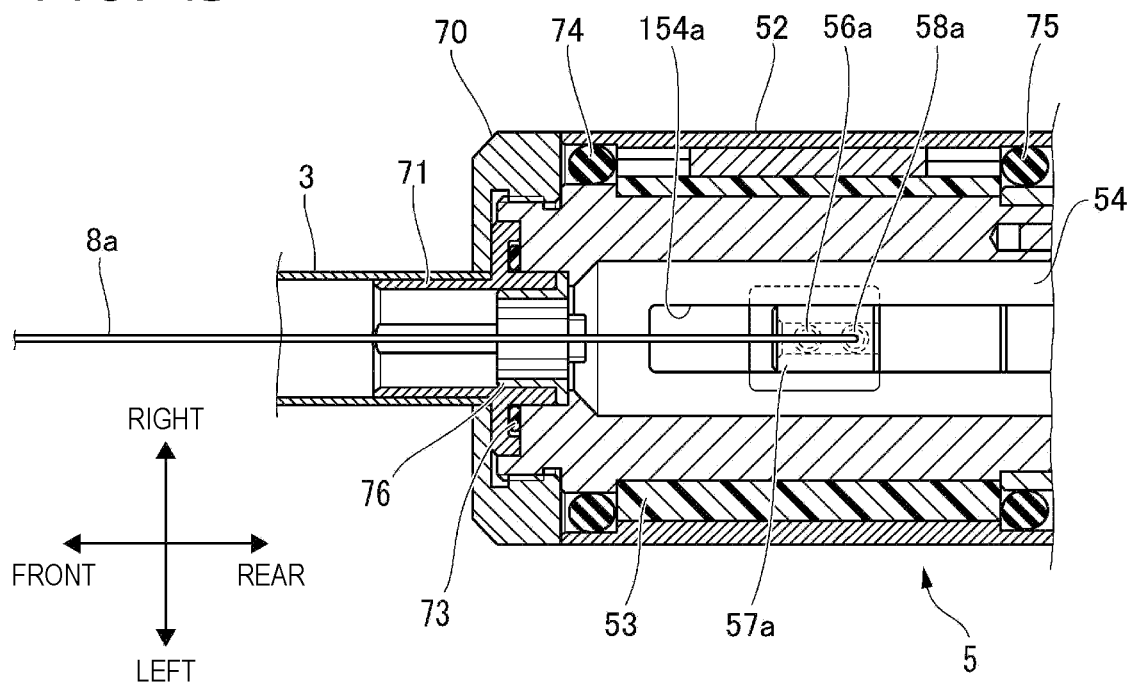
FIG. 4B is a cross-sectional view of the handle operation unit taken along a plane perpendicular to an up-down direction.

Next, a specific configuration of the handle operation unit 5 will be described below with reference to FIGS. 3 to 4B. FIG. 3 is an exploded perspective view of the handle operation unit 5. FIG. 4A is a cross-sectional view of the handle operation unit 5 taken along a plane perpendicular to the front-rear direction. FIG. 4B is a cross-sectional view of the handle operation unit 5 taken along a plane perpendicular to the up-down direction. As shown in FIG. 3, the handle operation unit 5 includes a body portion 50, an outer ring 52, a cam ring 53, a pair of slide members 55a and 55b, a support portion 54, a scope support portion 71, and a scope fixing portion 70. The handle operation unit 5 is configured to change a field of view of the image-capturing unit 2 in accordance with a rotation operation of a medical worker (the user) performed on the outer ring 52.

The body portion 50 is provided with a plurality of operation buttons 156a to 156d. The operation button 156a is an operation button configured to switching ON and OFF of light emitted from a light source. The operation button 156b is an operation button configured to change a state of a display screen displayed on a monitor connected to the endoscope 1. The operation buttons 156c and 156d are operation buttons configured to adjust intensity of the light emitted from the light source.

The outer ring 52 is a portion that is rotationally operated by the medical worker when changing the field of view of the image-capturing unit 2. Specifically, the movable portion 30 of the scope 3 can be inclined relative to the up-down direction by rotating the outer ring 52 clockwise or counterclockwise about a central axis Ax (see FIG. 5) extending in the front-rear direction of the handle operation unit 5. In this way, the field of view of the image-capturing unit 2 and an emission direction of light emitted from the light guide 4 can be adjusted according to the rotation of the outer ring 52 about the central axis Ax.

As shown in FIGS. 3 and 4B, the outer ring 52 is adjacent to the body portion 50 and the scope fixing portion 70, but is not fixed to the body portion 50 and the scope fixing portion 70. In a state where the handle operation unit 5 is assembled, a waterproof O-ring 75 is provided between the outer ring 52 and the body portion 50, and a waterproof O-ring 74 is provided between the outer ring 52 and the scope fixing portion 70. The outer ring 52 includes an engagement protrusion portion 152 that protrudes toward the cam ring 53.

As shown in FIGS. 3 and 4A, the cam ring 53 is accommodated in the outer ring 52 so as to rotate in accordance with the rotation of the outer ring 52 about the central axis Ax. The cam ring 53 is formed of, for example, a flexible resin material such as a plastic material. The cam ring 53 includes a pair of guide holes 153a and 153b that face each other. Each of the guide holes 153a and 153b extends in a direction inclined relative to the front-rear direction. In this regard, the guide holes 153a and 153b extend obliquely relative to the front-rear direction along an outer circumferential surface of the cam ring 53. In particular, the guide holes 153a and 153b extend obliquely each in a spiral shape. When an angular range of an entire circumference of the cam ring 53 is 360°, the guide holes 153a and 153b may extend over an angular range of 120° along the outer circumferential surface of cam ring 53. An inclination direction of the guide hole 153a and an inclination direction of the guide hole 153b may be the same.

The cam ring 53 includes an engagement recess portion 253 that engages the engagement protrusion portion 152 formed on the outer ring 52. Since the outer ring 52 and the cam ring 53 are engaged with each other via the engagement protrusion portion 152 and the engagement recess portion 253, the cam ring 53 can be reliably rotated in accordance with the rotation of the outer ring 52. In the present embodiment, the engagement recess portion may be provided in the outer ring 52 while the engagement protrusion portion is provided on the cam ring 53. In this case as well, the outer ring 52 and the cam ring 53 are engaged with each other.

The support portion 54 is configured to support the pair of slide members 55a and 55b, and is accommodated in the cam ring 53 (see FIG. 4A). The support portion 54 is provided with a pair of slide grooves 154a and 154b extending along the front-rear direction. The slide member 55a, which is disposed on an upper portion of the support portion 54, is slidable in the slide groove 154a. The slide member 55b, which is disposed on a lower portion of the support portion 54, is slidable in the slide groove 154b. The support portion 54 is fixed to each of the scope 3 and the body portion 50.

The slide member 55a is accommodated in the guide hole 153a and fixed to the upper wire 8a. The slide member 55a includes a slide pin 56a, a slide holder 57a, and a fixing pin 58a. The slide pin 56a is inserted into the guide hole 153a. The slide holder 57a holds the slide pin 56a and the fixing pin 58a, and is slidable in the slide groove 154a. The wire 8a is fixed to the slide holder 57a by the fixing pin 58a.

The slide member 55b is accommodated in the guide hole 153b and fixed to the lower wire 8b. The slide member 55b includes a slide pin 56b, a slide holder 57b, and a fixing pin 58b. The slide pin 56b is inserted into the guide hole 153b. The slide holder 57b holds the slide pin 56b and the fixing pin 58b, and is slidable in the slide groove 154b. The wire 8b is fixed to the slide holder 57b by the fixing pin 58b.

The scope support portion 71 is configured to support the scope 3 (see FIG. 1). As shown in FIG. 4B, the scope support portion 71 is inserted into a rear-end-side opening portion of the scope 3. A cap 76 is fitted into the scope support portion 71. A waterproof O-ring 73 is provided between the scope support portion 71 and the support portion 54. The scope 3 supported by the scope support portion 71 is fixed to the support portion 54 by the scope fixing portion 70.

Figure 5:
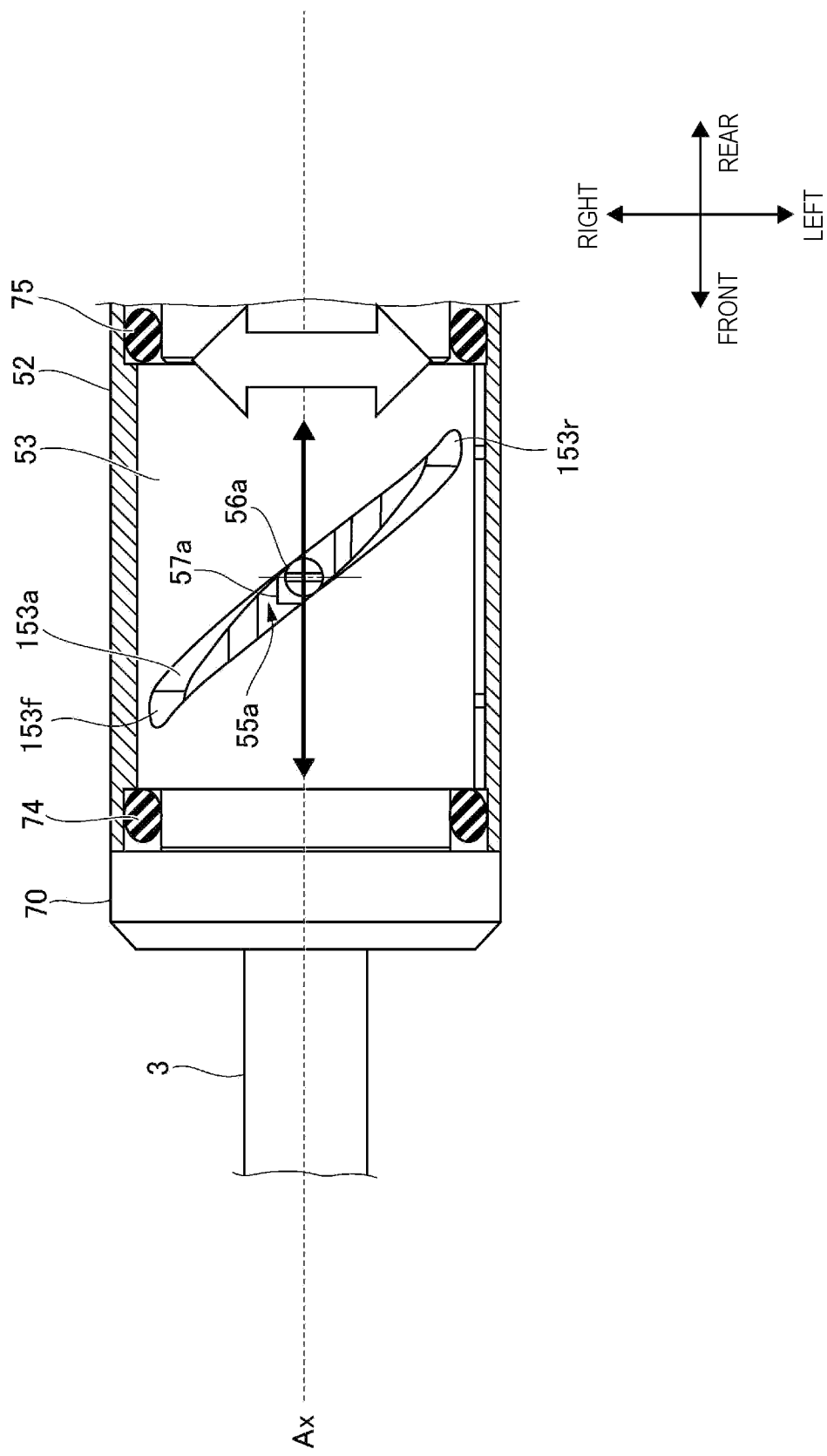
FIG. 5 shows a state where a slide pin moves in the front-rear direction in accordance with rotation of a cam ring.
Figure 6:
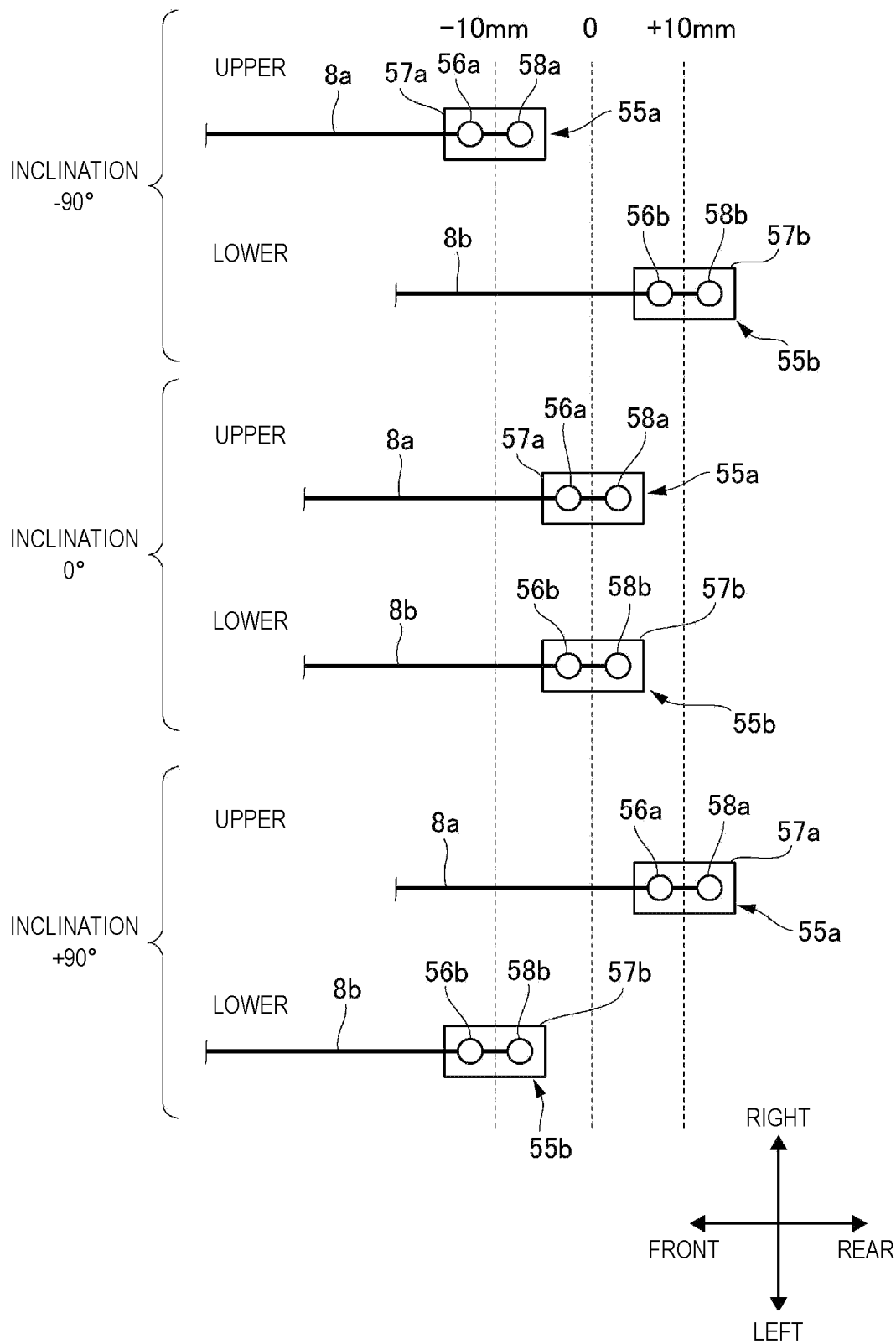
FIG. 6 shows a relationship between a positional relationship between an upper slide member and a lower slide member and an inclination angle of a movable portion of a scope.

Next, a principle of changing the field of view of the image-capturing unit 2 in accordance with the rotation of the outer ring 52 will be described below with reference to FIGS. 5 to 7B. FIG. 5 shows a state where the slide pin 56a moves in the front-rear direction in accordance with rotation of the cam ring 53. FIG. 6 shows a relationship between a positional relationship between the upper slide member 55a and the lower slide member 55b and an inclination angle of the movable portion 30 of the scope 3. FIG. 7A shows a state where the movable portion 30 of the scope 3 is inclined obliquely upward in accordance with counterclockwise rotation of the outer ring 52. FIG. 7B shows a state where the movable portion 30 of the scope 3 is inclined obliquely downward in accordance with clockwise rotation of the outer ring 52.

In the present embodiment, when the outer ring 52 is rotated about the central axis Ax of the handle operation unit 5 in response to a rotation operation of the user performed on the outer ring 52, the cam ring 53 engaged with the outer ring 52 is also rotated about the central axis Ax. As shown in FIG. 5, as the cam ring 53 rotates about the central axis Ax, the slide pin 56a inserted into the guide hole 153a is moved in the front-rear direction. Further, since the slide holder 57a holding the slide pin 56a slides in the slide groove 154a in the front-rear direction, the wire 8a fixed to the slide holder 57a is pulled or loosened.

Similarly to the above, as the cam ring 53 rotates about the central axis Ax, the slide pin 56b inserted into the guide hole 153b is moved in the front-rear direction. Further, since the slide holder 57b holding the slide pin 56b slides in the slide groove 154b in the front-rear direction, the wire 8b fixed to the slide holder 57b is pulled or loosened.

In this regard, since the cam ring 53 is formed of a flexible resin material, rotational movement of the cam ring 53 can be efficiently converted into linear movement of the slide pins 56a and 56b.

For example, when the outer ring 52 rotates clockwise, since a front end portion 153f of the guide hole 153a approaches the slide pin 56a, the slide pin 56a inserted into the guide hole 153a advances toward the forward direction (an example of a first direction). As a result, the wire 8a is loosened. On the other hand, when the outer ring 52 rotates clockwise, since a rear end portion of the guide hole 153b approaches the slide pin 56b, the slide pin 56b inserted into the guide hole 153b advances toward the rearward direction (an example of a second direction) that is opposite to the forward direction. As a result, the wire 8b is pulled toward the rearward direction. Although the guide hole 153b is not shown in FIG. 5, the guide hole 153b faces the guide hole 153a. In addition, a shape of the guide hole 153b overlaps a shape of the guide hole 153a in a top view.

In addition, when the outer ring 52 rotates counterclockwise, since a rear end portion 153r of the guide hole 153a approaches the slide pin 56a, the slide pin 56a inserted into the guide hole 153a advances toward the rearward direction. As a result, the wire 8a is pulled toward the rearward direction. On the other hand, when the outer ring 52 rotates counterclockwise, since a front end portion of the guide hole 153b approaches the slide pin 56b, the slide pin 56b inserted into the guide hole 153b advances toward the forward direction. As a result, the wire 8b is loosened.

In this way, when the outer ring 52 rotates clockwise, the wire 8a is loosened while the wire 8b is pulled. On the other hand, when the outer ring 52 rotates counterclockwise, the wire 8a is pulled while the wire 8b is loosened.

When the outer ring 52 does not rotate, neither of the wires 8a and 8b is pulled in the rearward direction. In this case, as shown in FIG. 1, the movable portion 30 of the scope 3 is parallel to the front-rear direction, and a field of view F of the image-capturing unit 2 faces the forward direction. As described above, when one of the wires 8a and 8b is pulled in the rearward direction, the movable portion 30 can be inclined relative to the up-down direction by the movable connection elements 301 to 304 provided on the movable portion 30.

For example, as shown in FIG. 7A, when the outer ring 52 rotates counterclockwise, the wire 8a is pulled in the rearward direction while the wire 8b is loosened. In this case, rearward tension acts on the fixing pin 130 fixed to the wire 8a, and the tension acts as a rotational moment for inclining the movable portion 30 upward. As a result, the movable portion 30 is inclined obliquely upward through the movable connection elements 301 to 304 shown in FIG. 1, and the field of view F of the image-capturing unit 2 accommodated in the movable portion 30 is changed. Specifically, the field of view F of the image-capturing unit 2 is changed from the forward direction to an obliquely upward direction.

In addition, as shown in FIG. 7B, when the outer ring 52 rotates clockwise, the wire 8a is loosened while the wire 8b is pulled in the rearward direction. In this case, rearward tension acts on the fixing pin 132 fixed to the wire 8b, and the tension acts as a rotational moment for inclining the movable portion 30 downward. As a result, the movable portion 30 is inclined obliquely downward through the movable connection elements 301 to 304. In this way, the field of view F of the image-capturing unit 2 is changed from the forward direction to an obliquely downward direction.

In addition, when the field of view F of the image-capturing unit 2 is changed, emission directions of the visible light and the excitation light emitted from the light guide 4 provided in the image-capturing unit 2 are also changed at the same time. In this way, it is possible to adjust the field of view F of the image-capturing unit 2 and the emission direction of the light emitted from the light guide 4 in accordance with the rotation operation of the outer ring 52.

As shown in a middle part of FIG. 6, when both the slide member 55a and the slide member 55b do not slide, an inclination angle between the front-rear direction and the movable portion 30 is 0°. That is, the movable portion 30 is parallel to the front-rear direction. At this time, a position of the slide member 55a and a position of the slide member 55b coincide with each other in the front-rear direction. In the following description, the positions of the slide members 55a and 55b in the front-rear direction when the inclination angle is 0° are defined as origins.

As shown in an upper part of FIG. 6, when the outer ring 52 rotates maximally in the clockwise direction, the slide member 55a is moved in the forward direction by 10 mm from the origin, and the slide member 55b is moved in the rearward direction by 10 mm from the origin. In this case, the inclination angle between the front-rear direction and the movable portion 30 is −90°, and the field of view F of the image-capturing unit 2 is directed to the downward direction. On the other hand, as shown in a lower part of FIG. 6, when the outer ring 52 rotates maximally in the counterclockwise direction, the slide member 55a is moved in the rearward direction by 10 mm from the origin, and the slide member 55b is moved in the forward direction by 10 mm from the origin. In this case, the inclination angle between the front-rear direction and the movable portion 30 is +90°, and the field of view F of the image-capturing unit 2 is directed to the upward direction. In this way, the inclination angle of the movable portion 30 can be adjusted within a range of 180° from +90° to −90° in accordance with the rotation operation of the outer ring 52. That is, according to the rotation operation of the outer ring 52, the field of view F of the image-capturing unit 2 and the emission direction of the light emitted from the light guide 4 can be adjusted within a range of 180° in the up-down direction. In addition, it is possible to finely adjust the field of view F of the image-capturing unit 2 according to an amount of the rotation operation of the outer ring 52.

According to the present embodiment, the pair of slide members 55a and 55b are slid in the slide grooves 154a and 154b by the rotation of the outer ring 52 in accordance with the operation of the user. Thereafter, one of the wire 8a fixed to the slide member 55a and the wire 8b fixed to the slide member 55b is pulled in the rearward direction. In this way, the movable portion 30 of the scope 3 is inclined relative to the up-down direction by tension applied to the wires 8a and 8b, and as a result, the field of view F of the image-capturing unit 2 is changed. Therefore, the user can relatively easily adjust the field of view F of the image-capturing unit 2 by an intuitive rotation operation performed on the handle operation unit 5. In addition, since it is not necessary to provide any field-of-view adjustment lever or the like for adjusting the field of view F of the image-capturing unit 2 in the handle operation unit 5, a size of the handle operation unit 5 can be reduced, and it is possible to further simplify and improve appearance of the handle operation unit 5. Further, since no field-of-view adjustment lever is provided in the handle operation unit 5, it is possible to prevent a situation where the field of view F of the image-capturing unit 2 is unintentionally changed due to unintended contact with the field-of-view adjustment lever. Therefore, the endoscope 1 and the handle operation unit 5 whose usability is further improved can be provided.

Although the movable portion 30 is inclined relative to the up-down direction in accordance with the rotation operation of the outer ring 52 in the present embodiment, the present embodiment is not limited thereto. In this regard, it is also possible to incline the movable portion 30 relative to the left-right direction in accordance with the rotation operation of the outer ring 52. In this case, the field of view F of the image-capturing unit 2 and the emission direction of the light can be adjusted within a range of 180° in the left-right direction in accordance with the inclination of the movable portion 30 relative to the left-right direction. For example, in a case where the scope 3 is fixed to the handle operation unit 5 in a state where the scope 3 is rotated by 90° about the central axis of the scope 3, the movable portion 30 can be inclined relative to the left-right direction in accordance with the rotation operation of the outer ring 52. When the scope 3 is rotated about the central axis by 90°, the support portion 54 and the cam ring 53 are also rotated about the central axis by 90°. In addition, when the medical worker uses the endoscope 1 in a state where the handle operation unit 5 is rotated by 90° relative to the central axis, the movable portion 30 is inclined relative to the left-right direction, and thus the field of view F of the image-capturing unit 2 and the emission direction of the light can be inclined relative to the left-right direction.

In addition, although the field of view F of the image-capturing unit 2 accommodated in the movable portion 30 is changed by pulling one of the wires 8a and 8b in the rearward direction in the present embodiment, the present embodiment is not limited thereto. For example, the field of view F of the image-capturing unit 2 may also be changed by inclining an optical member fixed to the wires 8a and 8b relative to the up-down direction. Here, the optical member is a lens or a prism configured to guide the light reflected by the biological tissue toward the image sensor. In this case, the field of view F of the image-capturing unit 2 can be changed by inclining the optical member accommodated in the movable portion 30 by the wires 8a and 8b while the movable portion 30 is not inclined relative to the up-down direction. In this way, it is also possible to change the field of view F of the image-capturing unit 2 without inclining the entire movable portion 30.

Although the embodiment of the present invention have been described above, it is needless to say that the technical scope of the present invention should not be construed as being limited by the description of the embodiment. It is to be understood by those skilled in the art that the present embodiment is merely an example, and various modifications of the embodiment are possible within the scope of the invention described in the claims. The technical scope of the present invention should be determined based on the scope of the invention described in the claims and the scope of equivalents thereof.

What is claimed is:
1. An endoscope comprising:
    a scope;
    an image sensor accommodated in the scope, the image sensor being configured to capture an image of an object;
    a handle configured to change a field of view of the image sensor in accordance with an operation of a user; and
    a force transmission member accommodated in the scope and fixed to the handle and the scope,
    wherein the handle comprises:
        an outer ring configured to be operated by the user;
        a cam ring accommodated in the outer ring so as to rotate in accordance with rotation of the outer ring about a central axis of the handle, the cam ring having a pair of guide holes;
        a pair of slide members, each of the pair of slide members being accommodated in a corresponding one of the pair of guide holes and fixed to the force transmission member; and a support portion having a pair of slide grooves extending along a longitudinal direction of the endoscope, the support portion being accommodated in the cam ring to support the pair of slide members,
wherein each of the pair of slide members is slidable in a corresponding one of the pair of slide grooves,
wherein each of the pair of slide members slides in the corresponding one of the pair of slide grooves in accordance with the rotation of the outer ring about the central axis,
wherein the field of view of the image sensor is changed in accordance with sliding of the pair of slide members, and
wherein each of the pair of slide members comprises:
a slide pin accommodated in the corresponding one of the pair of guide holes; and
a slide holder holding the slide pin, the slide holder being slidable in the corresponding one of the pair of slide grooves.

2. The endoscope according to claim 1,
wherein the scope comprises a movable portion configured to be inclined relative to an up-down direction or a left-right direction perpendicular to the longitudinal direction,
wherein the image sensor is accommodated in the movable portion,
wherein the force transmission member is fixed to the movable portion,
wherein the movable portion is inclined relative to the up-down direction or the left-right direction in accordance with sliding of the pair of slide members, and
wherein the field of view of the image sensor is changed in accordance with inclination of the movable portion.

3. The endoscope according to claim 1,
wherein as the cam ring rotates, one of the pair of slide members slides in one of the pair of slide grooves in a first direction while another of the pair of slide members slides in another of the pair of slide grooves in a second direction that is opposite to the first direction.

4. The endoscope according to claim 3,
wherein when the one of the pair of slide members slides in the first direction in the one of the pair of slide grooves, the force transmission member fixed to the one of the pair of slide members is pulled in the first direction, and
wherein when the other of the pair of slide members slides in the second direction in the other of the pair of slide grooves, the force transmission member fixed to the other of the pair of slide members is loosened.

5. The endoscope according to claim 1,
wherein the pair of guide holes extend along a direction that is inclined relative to the longitudinal direction of the endoscope.

6. The endoscope according to claim 1,
wherein the slide holder is fixed to the force transmission member.

7. The endoscope according to claim 1,
wherein one of the outer ring and the cam ring comprises an engagement protrusion portion protruding toward another of the outer ring and the cam ring, and
wherein the other of the outer ring and the cam ring has an engagement recess portion configured to engage the engagement protrusion portion.

8. The endoscope according to claim 1,
wherein the image sensor is configured to generate image data of the object, and
wherein an optical member is optically connected to the image sensor, the optical member being configured to guide light associated with the object to the image sensor.

9. The endoscope according to claim 8,
further comprising a light emitter configured to emit light toward the object,
wherein the field of view of the image sensor and an emission direction of the light emitted from the light emitter are changed in accordance with the rotation of the outer ring about the central axis.

10. An endoscope comprising:
a scope;
an image sensor accommodated in the scope, the image sensor being configured to capture an image of an object;
a handle configured to change a field of view of the image sensor in accordance with an operation of a user; and
a force transmission member accommodated in the scope and fixed to the handle,
wherein the handle comprises:
an outer ring configured to be operated by the user;
a cam ring accommodated in the outer ring so as to rotate in accordance with rotation of the outer ring about a central axis of the handle, the cam ring having a pair of guide holes;
a pair of slide members, each of the pair of slide members being accommodated in a corresponding one of the pair of guide holes and fixed to the force transmission member; and
a support portion having a pair of slide grooves extending along a longitudinal direction of the endoscope, the support portion being accommodated in the cam ring to support the pair of slide members,
wherein each of the pair of slide members is slidable in a corresponding one of the pair of slide grooves,
wherein each of the pair of slide members slides in the corresponding one of the pair of slide grooves in accordance with the rotation of the outer ring about the central axis,
wherein the field of view of the image sensor is changed in accordance with sliding of the pair of slide members, and
wherein each of the pair of slide members comprises:
a slide pin accommodated in the corresponding one of the pair of guide holes; and
a slide holder holding the slide pin, the slide holder being slidable in the corresponding one of the pair of slide grooves.

11. A handle configured to change a field of view of an endoscope in accordance with an operation of a user, the handle comprising:
an outer ring configured to be operated by the user;
a cam ring accommodated in the outer ring so as to rotate in accordance with rotation of the outer ring about a central axis of the handle, the cam ring having a pair of guide holes;
a pair of slide members, each of the pair of slide members being accommodated in a corresponding one of the pair of guide holes and fixed to a force transmission member; and
a support portion having a pair of slide grooves extending along a longitudinal direction of the endoscope, the support portion being accommodated in the cam ring to support the pair of slide members,
wherein each of the pair of slide members is slidable in a corresponding one of the pair of slide grooves, wherein each of the pair of slide members slides in the corresponding one of the pair of slide grooves in accordance with the rotation of the outer ring about the central axis, wherein the field of view of the endoscope is changed in accordance with sliding of the pair of slide members, and wherein each of the pair of slide members comprises:
- a slide pin accommodated in the corresponding one of the pair of guide holes; and
- a slide holder holding the slide pin, the slide holder being slidable in the corresponding one of the pair of slide grooves.

12. The endoscope according to claim 1, wherein the scope comprises a tube, the tube having a base end and a distal end, wherein the force transmission member is accommodated in the tube through the base end and fixed to the handle and the tube, wherein a position of the tube at which the force transmission member is fixed is farther from the distal end than the image sensor, and wherein in accordance with sliding of the pair of slide members, a part of the tube, including the position of the tube, is caused to be inclined and the field of view of the image sensor is changed.

* * * * *